(12) United States Patent
Bagambisa

(10) Patent No.: US 8,235,721 B2
(45) Date of Patent: Aug. 7, 2012

(54) DENTAL IMPLANTS FOR IMPLANTATION IN A HUMAN OR ANIMAL JAWBONE AND METHODS OF MANUFACTURING SAME

(75) Inventor: Frank Bagambisa, Bonn (DE)

(73) Assignee: Frank Bagambisa (DE)

( * ) Notice: Subject to any disclaimer, the term of this patent is extended or adjusted under 35 U.S.C. 154(b) by 127 days.

(21) Appl. No.: 12/565,547

(22) Filed: Sep. 23, 2009

(65) Prior Publication Data

US 2010/0086898 A1    Apr. 8, 2010

(30) Foreign Application Priority Data

Sep. 25, 2008   (DE) .................... 10 2008 049 014

(51) Int. Cl.
*A61C 8/00* (2006.01)
(52) U.S. Cl. ..................................... 433/173; 433/201.1
(58) Field of Classification Search .................. 433/173, 433/174, 201.1
See application file for complete search history.

(56) References Cited

U.S. PATENT DOCUMENTS

| | | | | |
|---|---|---|---|---|
| 5,980,252 A * | 11/1999 | Samchukov et al. | ......... | 433/215 |
| 6,089,867 A * | 7/2000 | Filho | ............................. | 433/215 |
| 6,126,662 A * | 10/2000 | Carmichael et al. | .......... | 606/916 |
| 6,589,525 B2 * | 7/2003 | Gault | ........................... | 424/93.7 |
| 7,033,359 B2 * | 4/2006 | Meller | ............................ | 606/80 |
| 7,179,084 B1 * | 2/2007 | Kometas | ........................ | 433/75 |
| 2005/0053585 A1 * | 3/2005 | Black et al. | .................. | 424/93.7 |
| 2009/0305189 A1 * | 12/2009 | Scortecci et al. | ............. | 433/165 |

* cited by examiner

*Primary Examiner* — Ralph Lewis
(74) *Attorney, Agent, or Firm* — Hanley, Flight & Zimmerman, LC

(57) ABSTRACT

The subject matter of the invention is, in one example, a dental implant for implantation in a human or animal jawbone with an implant for receiving a dental prosthesis. Providing a dental implant that can be implanted with less discomfort for the patient is achieved in that the implant is at least in parts surrounded with bone substance of the patient, said bone substance not originating from the place in the jaw of the patient at which the dental implant is intended to be implanted.

20 Claims, 5 Drawing Sheets

DENTAL IMPLANTS FOR IMPLANTATION IN A HUMAN OR ANIMAL JAWBONE AND METHODS OF MANUFACTURING SAME

TECHNICAL FIELD

The present invention relates to dental implants and, more particularly to dental implants for implantation in a human or animal jawbone and methods of manufacturing the same.

BACKGROUND

To replace missing teeth, it belongs to prior art to implant into the jawbone artificial dental implants made from titanium, ceramics or from another suited material. A prerequisite therefor however is that the jawbone has sufficient healthy bone substance at the place of implantation for the dental implant to be sufficiently held when implanted. If there is no sufficient healthy bone substance, bone substance can be built up at the place of implantation by removing bone from another area and by grafting it at the place of implantation. However, this process is very time intensive since the transplanted bone substance must first grow into the jawbone before the dental implant can be implanted. During this time, the patient cannot use this tooth region. After the transplanted bone substance has grown in, the patient must undergo another intervention for implanting the actual dental implant.

DETAILED DESCRIPTION

Figure 1:
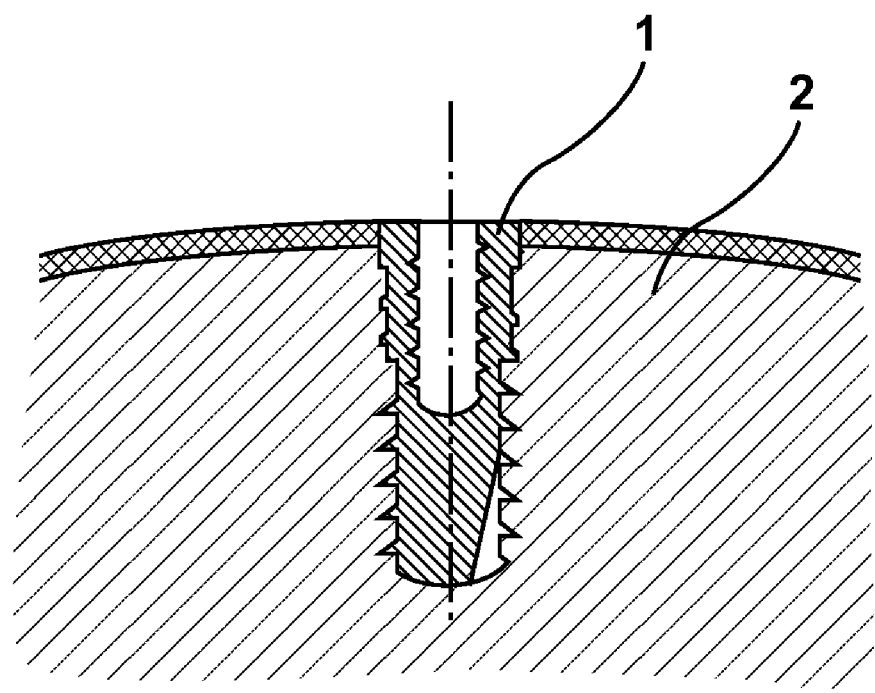
FIG. 1 shows a conventional implant in any bone of the patient.

In the FIGS. 1 through 5, an example procedure of such an implantation of an example dental implant is shown by way of example. This procedure will be described in closer detail herein after:

On patients with insufficient bone substance at the place of implantation in the jaw, the implant 1 needed for dental prosthesis can first be implanted in conventional manner at a suited location in the body of the patient. This may for example be a pelvic bone 2. FIG. 1 shows a commercially available implant 1 that has been implanted into a pelvic bone 2.

Figure 2:
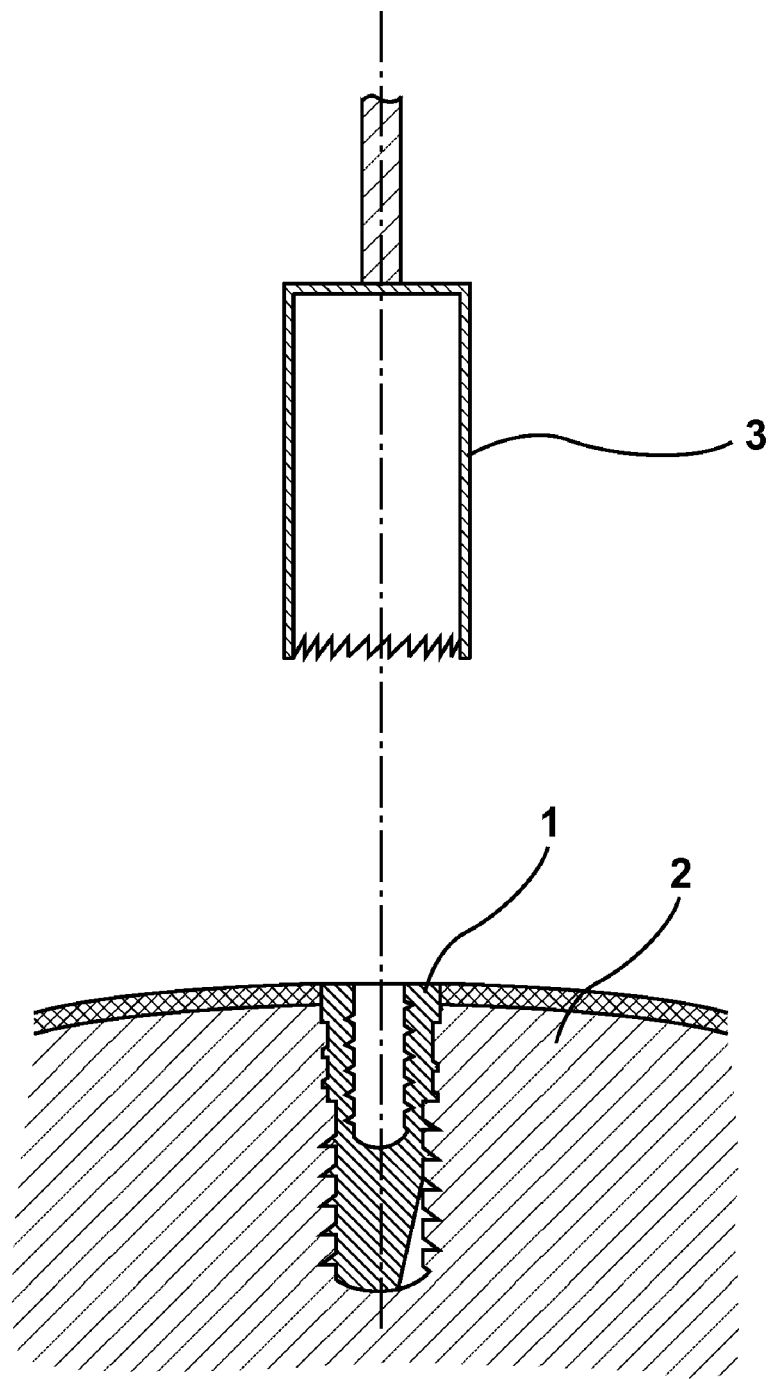
FIG. 2 is an exploded view of a trephine bur and of the implant shown in FIG. 1, shortly before explantation of the dental implant.
Figure 3:
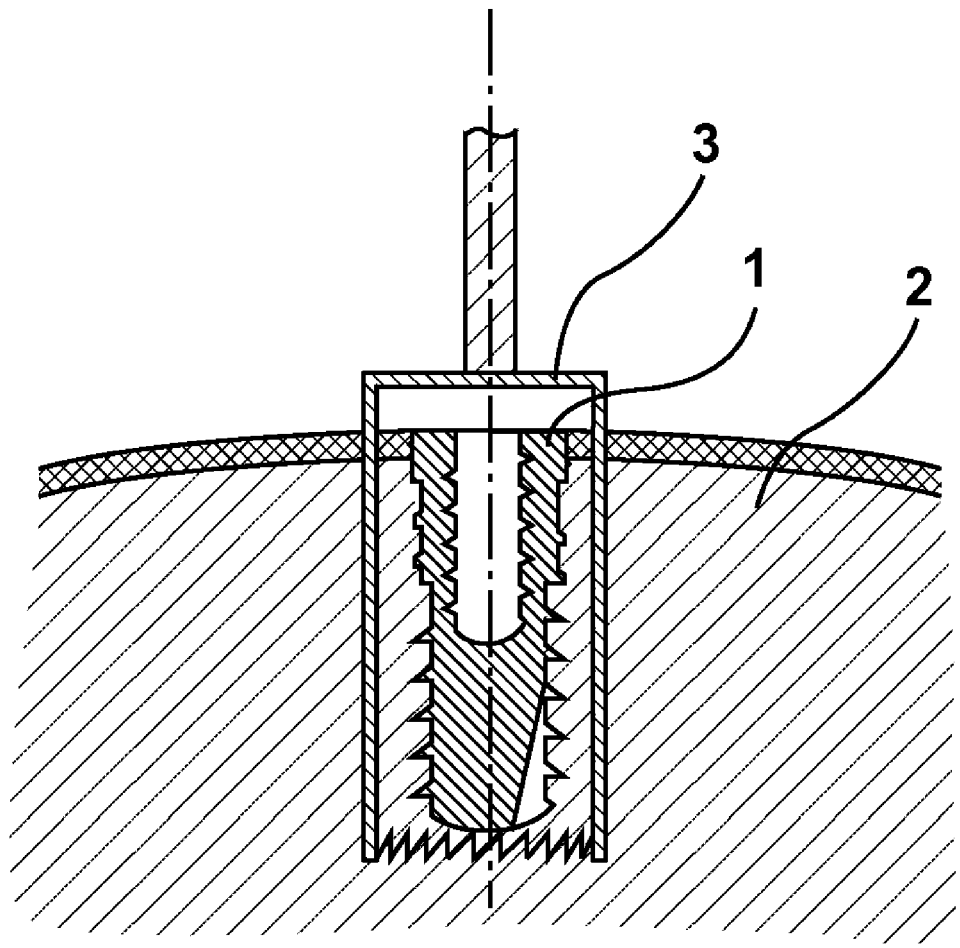
FIG. 3 is an exploded view of the trephine bur and of the implant shown in FIG. 2 after the trephine bur has drilled out the dental implant.
Figure 4:
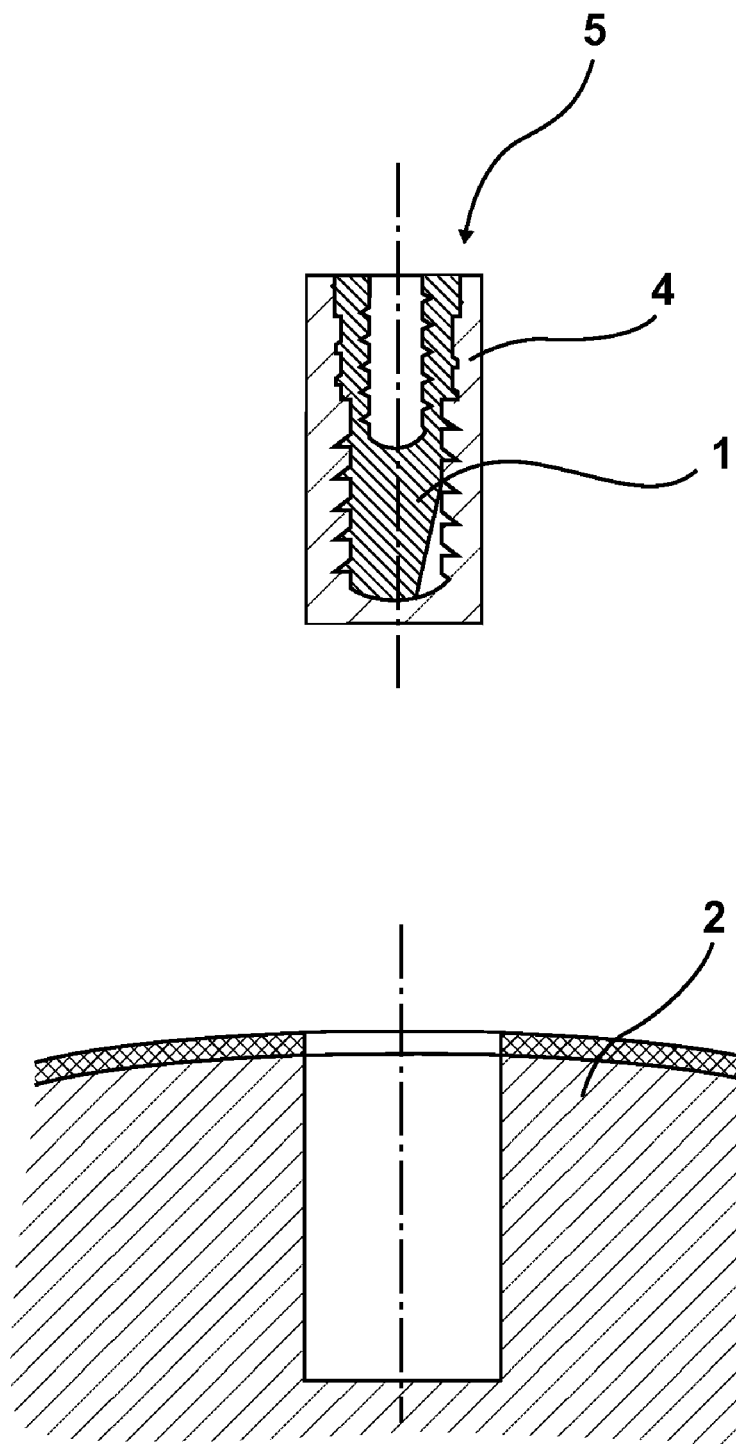
FIG. 4 is an exploded view of an example dental implant described herein and of the bone shown in FIG. 3.
Figure 5:
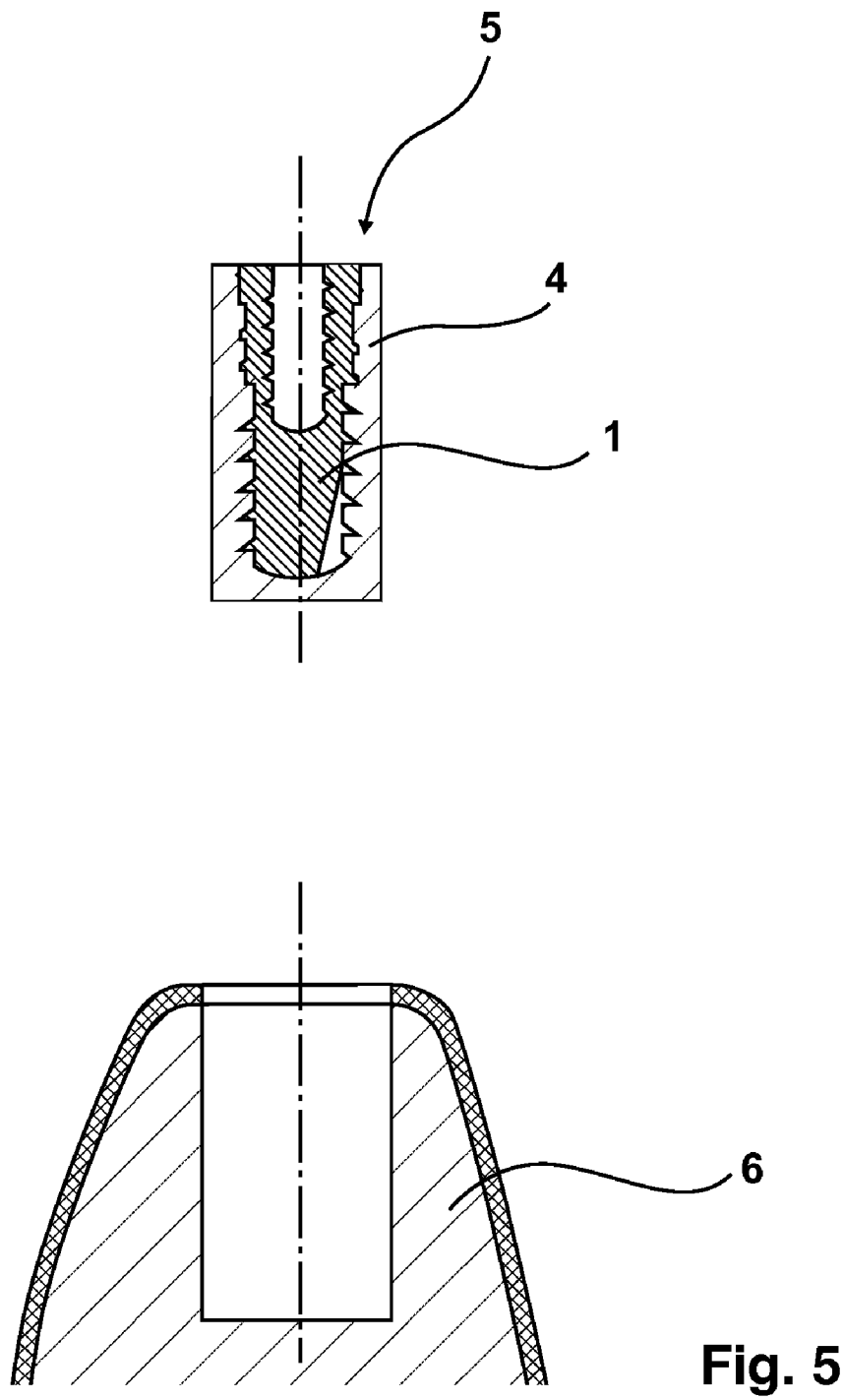
FIG. 5 is an exploded view of the example dental implant described herein shortly before implantation at the desired location in the jawbone of the patient.

The actual dental implant 5 is provided by drilling the implant 1 together with the bone substance 4 surrounding the implant 1 out of the pelvic bone 2 using a trephine bur 3 as shown in the FIGS. 2 and 3. The clear diameter of the trephine bur 3 is chosen so that it is between 1 millimeters (mm) and 8 mm, in the example described herein 3 mm, larger than the largest outer diameter of the implant 1. This appears in particular from FIG. 3. As a result, the implant 1 is explanted together with the bone substance 4 surrounding the implant 1, as shown in FIG. 4. The bone substance 4 is disposed in the approximate shape of a bushing on the substantially cylindrical sheath of the implant 1 and has a wall thickness of 1.5 mm in this example.

The thus made dental implant 5, which incorporates the implant 1 and the bone substance 4, is then implanted into a correspondingly prepared location in the jawbone 6 of the patient where ingrowth can take place. Advantageously, the recess made in the jawbone 6 should be chosen to be large enough for the dental implant to fit in the recess (together with the bone substance 4).

In the example shown herein, the dental implant 5 can be explanted immediately after the implant 1 has been implanted into the pelvic bone 2.

In view of the foregoing, the examples described herein may provide a dental implant of the type mentioned herein above that can be implanted with less discomfort for the patient. The inventions, as defined by the claims appended hereto, provide advantageous developed implementations of these dental implants and methods.

The example dental implants configured according to this technical teaching and methods carried out according to this technical teaching offer the advantage that the bone substance needed for building up the bone is implanted together with the actual implant, said bone substance being removed in one piece from another bone of the patient. As a result, the cumbersome and time-intensive bone buildup is no longer necessary so that the patient will be able to chew much faster. In particular if the dental implant is explanted immediately after having been implanted into a bone of the patient and is next implanted in the jaw, the entire implantation can be performed in one single intervention. This saves the patient from an intervention, especially for building up the bone substance.

In some examples, it has proved advantageous to provide about the dental implant bone substance having a wall thickness ranging from 0.5 mm to 4 mm, bone substance having a wall thickness ranging from 1 mm to 2 mm being sufficient in many cases. The advantage thereof is that sufficient bone substance is implanted about the dental implant at the critical place in the jaw of the patient so that the dental implant finds sufficient hold after bone ongrowth.

In another example that has not been shown herein, it is also possible to leave the implant in the pelvic bone until ongrowth of the bone substance to the implant has occurred before the dental implant is drilled out of the pelvic bone together with the ongrown bone substance.

This patent application makes reference to, incorporates the same herein by reference, and claims all benefits accruing under 35 U.S.C. §119 from an application for patent filed in the German Patent Office on Sep. 25, 2008, and there assigned Serial No. DE 10 2008 049 014.8.

Further advantages of the dental implants and methods described herein are apparent. Likewise, the invention lies in each and every novel feature or combination of features mentioned above or described herein after. The embodiments discussed herein are merely exemplary in nature and are not intended to limit the scope of the invention in any manner. The examples provided are not intended to limit the scope of the invention in any manner. Although certain example apparatus, methods, and articles of manufacture are described herein, other implementations are possible. The scope of coverage of this patent is not limited to the specific examples described herein. On the contrary, this patent covers all apparatus, methods, and articles of manufacture falling within the scope of the invention.

The invention claimed is:

1. A method of creating a dental implant assembly for implantation into a jawbone of a patient, the method comprising:
   implanting an implant at a first location in a bone of a body of the patient, the first location different than a place in the jawbone of the patient where the dental implant assembly is intended to be implanted;
   explanting the implant and a layer bone substance from the bone surrounding the implant for implantation of the implant and the layer of the bone substance at the place in the jawbone of the patient; and
   implanting the implant and the bone substance in the place of the jawbone.

2. The method as set forth in claim 1, wherein explanting the implant comprising explanting the implant immediately after the implanting at the first location.

3. The method as set forth in claim 1, wherein explanting the implant comprises explanting the implant after the bone substance has grown onto the dental implant.

4. The method as set forth in claim 1, wherein explanting the implant comprises using a trephine bur to explant the implant.

5. The method of claim 4, wherein the trephine bur has a diameter larger than a largest outer diameter of the implant.

6. The method of claim 4, wherein the trephine bur has a diameter of about 3 mm larger than the implant.

7. The method as set forth in claim 1, wherein the explanted bone substance has wall thickness of about 1.5 mm.

8. The method as set forth in claim 1, wherein the bone substance adheres loosely to the implant.

9. The method as set forth in claim 1, wherein the patient is a human or an animal.

10. The method as set forth in claim 1, wherein the bone substance has an approximate shape of a bushing on a cylindrical sheath of the implant.

11. The method as set forth in claim 1, wherein the implant has a plurality of extensions to extend into the bone substance.

12. The method as set forth in claim 1, wherein the implant has a central bore.

13. The method as set forth in claim 1, wherein the bone substance has a wall thickness ranging from about 0.5 mm to about 4 mm.

14. The method as set forth in claim 1, wherein the bone substance has a wall thickness ranging from about 1 mm to about 2 mm.

15. The method as set forth in claim 1, wherein the first location is a location on a pelvic bone.

16. A method of creating a dental implant assembly for implantation into a jawbone of a patient, the method comprising:
   implanting an implant at a pelvic bone of a body of the patient; and
   explanting the implant and a layer bone substance from the pelvic bone surrounding the implant for implantation of the implant and the layer of the bone substance in the jawbone of the patient.

17. The method as set forth in claim 16, wherein the bone substance has a wall thickness ranging from about 0.5 mm to about 4 mm.

18. The method as set forth in claim 17, wherein the bone substance has a wall thickness of about 1.5 mm.

19. The method as set forth in claim 16, wherein the bone substance has grown onto the implant.

20. The method as set forth in claim 16, wherein explanting the implant comprises using a trephine bur to explant the implant.

* * * * *